United States Patent [19]
Stewart

[11] Patent Number: 6,040,430
[45] Date of Patent: Mar. 21, 2000

[54] NUCLEIC ACID ENCODING SITE SPECIFIC RECOMBINASE AND NUCLEAR RECEPTOR FUSION PROTEIN

[75] Inventor: Francis Stewart, Gaiberg, Germany

[73] Assignee: European Molecular Biology Laboratory (EMBL), Heidelberg, Germany

[21] Appl. No.: 08/564,264

[22] PCT Filed: Jun. 28, 1994

[86] PCT No.: PCT/EP94/02088

§ 371 Date: Dec. 26, 1995

§ 102(e) Date: Dec. 26, 1995

[87] PCT Pub. No.: WO95/00555

PCT Pub. Date: Jan. 5, 1995

[30] Foreign Application Priority Data

Jun. 28, 1993 [EP] European Pat. Off. .............. 93110298

[51] Int. Cl.$^7$ ...................... C07K 14/435; C07K 14/705; C12N 15/12; C12N 15/62
[52] U.S. Cl. ........................ 530/358; 435/69.1; 435/69.7; 435/195; 435/320.1; 435/325; 435/7.1; 435/18; 530/350; 536/23.2; 536/23.4; 536/23.5
[58] Field of Search ..................... 530/350, 358; 435/7.1, 69.1, 320.1, 240.2, 325, 6, 69.7, 195; 536/23.1, 23.2, 23.3, 23.5

[56] References Cited

U.S. PATENT DOCUMENTS

5,434,066  7/1995  Bebee et al. ......................... 435/172.3
5,589,362  12/1996  Bujard et al. .......................... 435/69.1

FOREIGN PATENT DOCUMENTS

0 146 050  6/1985  European Pat. Off. .

OTHER PUBLICATIONS

Gossen et al. (1992) Proc. Natl. Acad. Sci. USA 89:5547–5551.
Logie et al. (1995) Proc. Natl. Acad. Sci USA 92:5940–5944.
Metzger et al. (1995) Proc. Natl. Acad. Sci. USA 92:6991–6995.
Yu et al. (1991) Cell 67:1251–1266.
Stark et al., Trends in Genetics, "Catalysis by site–specific recombinases", vol. 8, 1992, pp. 432–439.
Boehmelt et al., The EMBO Journal, "Hormone–regulated v–rel estrogen receptor fusion protein: . . . ", vol. 11, No. 12, pp. 4641–4652.
Sauer et al., Nucleic Acids Research, "Cre–stimulated recombination . . . ", vol. 17, No. 1, pp. 147–161.
Chen et al., Nucleic Acids Research, "Sequence organization of the circular plasmid pKD1 . . . ", vol. 14, No. 11, pp. 4471–4481.
Picard et al., Cell, "A moveable and regulable inactivation function . . . ", vol. 54, pp. 1073–1080.
Superti–Furga et al., Proceedings of the National Academy of Sciences of The United States of America, "Hormone–dependent transcriptional regulation . . . ", vol. 88, No. 12, pp. 5114–5118.

*Primary Examiner*—Stephen Walsh
*Assistant Examiner*—Michael Pak
*Attorney, Agent, or Firm*—Nikaido Marmelstein Murray & Oram, LLP

[57] ABSTRACT

An invention is described that permits the regulation of recombination in cells, organisms or appropriate cell-free systems. The invention involves creating fusion proteins between recombinase proteins, or components of recombinase systems, and ligand binding domains derived from nuclear receptors. The fusion proteins show little recombinase activity in the absence of the ligand that binds to the ligand binding domain. Upon binding of the ligand, recombinase activity is induced. The invention provides a practical means to regulate recombination in cells and organisms and, by linking ligand binding to recombination, provides a simple means whereby ligand binding can be measured as recombination achieved.

15 Claims, 6 Drawing Sheets

FLP/EBD AMINO ACID SEQUENCE AS ENCODED BY PHFE1

1   MPQFDILCKT PPKVLVRQFV ERFERPSGEK IALCAAELTY LCWMITHNGT

51  AIKRATFMSY NTIISNSLSL DIVNKSLQFK YKTQKATILE ASLKKLIPAW

101 EFTIIPYYGQ KHQSDITDIV SSLQLQFESS EEADKGNSHS KKMLKALLSE

151 GESIWEITEK ILNSFEYTSR FTKTKTLYQF LFLATFINCG RFSDIKNVDP

201 KSFKLVQNKY LGVIIQCLVT ETKTSVSRHI YFFSARGRID PLVYLDEFLR

251 NSEPVLKRVN RTGNSSSNKQ EYQLLKDNLV RSYNKALKKN APYSIFAIKN

301 GPKSHIGRHL MTSFLSMKGL TELTNVVGNW SDKRASAVAR TTYTHQITAI

351 PDHYFALVSR YYAYDPISKE MIALKDETNP IEEWQHIEQL KGSAEGSIRY

401 PAWNGIISQE VLDYLSSYIN RRI

- FLP ENDS HERE -

424 SVRGS

- LINKER PEPTIDE ENDS HERE -

429 MK GGIRKDRRGG RMLKHKRQRD

451 DGEGRGEVGS AGDMRAANLW PSPLMIKRSK KNSLALSLTA DQMVSALLDA

501 EPPILYSEYD PTRPFSEASM MGLLTNLADR ELVHMINWAK RVPGFVDLTL

551 HDQVHLLECA WLEILMIGLV WRSMEHPVKL LFAPNLLLDR NQGKCVEGMV

601 EIFDMLLATS SRFRMMNLQG EEFVCLKSII LLNSGVYTFL SSTLKSLEEK

651 DHIHRVLDKI TDTLIHLMAK AGLTLQQQHQ RLAQLLLILS HIRHMSNKGM

701 EHLYSMKCKN VVPLYDLLLE MLDAHRLHAP TSRGGASVEE TDQSHLATAG

751 STSSHSLQKY YITGEAEGFP ATV

- ESTROGEN BINDING DOMAIN ENDS HERE -

Fig. 4/1

CODING SEQUENCE OF THE FLP/EBD FUSION PROTEIN ENCODED BY PHFE1

ATGCCACAATTTGATATATTATGTAAAACACCACCTAAGGTGCTTGTTCGT
CAGTTTGTGGAAAGGTTTGAAAGACCTTCAGGTGAGAAAATAGCATTATG
TGCTGCTGAACTAACCTATTTATGTTGGATGATTACACATAACGGAACAGC
AATCAAGAGAGCCACATTCATGAGCTATAATACTATCATAAGCAATTCGC
TGAGTTCCGATATTGTCAACAAGTCACTGCAGTTTAAATACAAGACGCAA
AAAGCAACAATTCTGGAAGCCTCATTAAAGAAATTGATTCCTGCTTGGGA
ATTTACAATTATTCCTTACTATGGACAAAAACATCAATCTGATATCACTG
ATATTGTAAGTAGTTTGCAATTACAGTTCGAATCATCGGAAGAAGCAGAT
AAGGGAAATAGCCACAGTAAAAAAATGCTTAAAGCACTTCTAAGTGAGG
GTGAAAGCATCTGGGAGATCACTGAGAAATACTAAATTCGTTTGAGTAT
ACTTCGAGATTTACAAAAACAAAAACTTTATACCAATTCCTCTTCCTAGC
TACTTTCATCAATTGTGGAAGATTCAGCGATATTAAGAACGTTGATCCGA
AATCATTTAAATTAGTCCAAAATAAGTATCTGGGAGTAATAATCCAGTG
TTTAGTGACAGAGACAAAGACAAGCGTTAGTAGGCACATATACTTCTTTA
GCGCAAGGGGTAGGATCGATCCACTTGTATATTTGGATGAATTTTTGAGGA
ATTCTGAACCAGTCCTAAAACGAGTAAATAGGACCGGCAATTCTTCAAGC
AACAAGCAGGAATACCAATTATTAAAAGATAACTTAGTCAGATCGTACA
ACAAAGCTTTGAAGAAAATGCGCCTTATTCAATCTTTGCTATAAAAAA
TGGCCCAAAATCTCACATTGGAAGACATTTGATGACCTCATTTCTTTCAAT
GAAGGGCCTAACGGAGTTGACTAATGTTGTGGGAAATTGGAGCGATAAGCG
TGCTTCTGCCGTGGCCAGGACAACGTATACTCATCAGATAACAGCAATACCT
GATCACTACTTCGCACTAGTTTCTCGGTACTATGCATATGATCCAATATCA
AAGGAAATGATAGCATTGAAGGATGAGACTAATCCAATTGAGGAGTGGC
AGCATATAGAACAGCTAAAGGGTAGTGCTGAAGGAAGCATACGATACCCC
GCATGGAATGGGATAATATCACAGGAGGTACTAGACTACCTTTCATCCTAC
ATAAATAGACGCATA

-FLP ENDS HERE-

TCCGTACGCGGATCC

- SYNTHETIC LINKER SEQUENCE ENDS HERE -

ATGAAAGGTGGGATACGAAAGACCGAAGAGGAGGGAGAATGTTGAAAC
ACAAGCGCCAGAGAGATGATGGGGAGGGCAGGGGTGAAGTGGGGTCTGCTG
GAGACATGAGAGCTGCCAACCTTTGGCCAAGCCCGCTCATGATCAAACGCTC
TAAGAAGAACAGCCTGGCCTTGTCCCTGACGGCCGACCAGATGGTCAGTGCCT
TGTTGGATGCTGAGCCCCCATACTCTATTCCGAGTATGATCCTACCAGACCC
TTCAGTGAAGCTTCGATGATGGGCTTACTGACCAACCTGGCAGACAGGGAGC
TGGTTCACATGATCAACTGGGCGAAGAGGGTGCCAGGCTTTGTGGATTTGAC

Fig. 4/2

```
CCTCCATGATCAGGTCCACCTTCTAGAATGTGCCTGGCTAGAGATCCTGATG
ATTGGTCTCGTCTGGCGCTCCATGGAGCACCCAGTGAAGCTACTGTTTGCTCCT
AACTTGCTCTTGGACAGGAACCAGGGAAAATGTGTAGAGGGCATGGTGGAG
ATCTTCGACATGCTGCTGGCTACATCATCTCGGTTCCGCATGATGAATCTGCA
GGGAGAGGAGTTTGTGTGCCTCAAATCTATTATTTTGCTTAATTCTGGAGTG
TACACATTTCTGTCCAGCACCCTGAAGTCTCTGGAAGAGAAGGACCATATCC
ACCGAGTCCTGGACAAGATCACAGACACTTTGATCCACCTGATGGCCAAGGC
AGGCCTGACCCTGCAGCAGCAGCACCAGCGGCTGGCCCAGCTCCTCCTCATCCT
CTCCCACATCAGGCACATGAGTAACAAAGGCATGGAGCATCTGTACAGCAT
GAAGTGCAAGAACGTGGTGCCCCTCTATGACCTGCTGCTGGAGATGCTGGAC
GCCCACCGCCTACATGCGCCCACTAGCCGTGGAGGGGCATCCGTGGAGGAGAC
GGACCAAAGCCACTTGGCCACTGCGGGCTCTACTTCATCGCATTCCTTGCAAA
AGTATTACATCACGGGGGAGGCAGAGGGTTTCCCTGCCACAGTCTGA
```

- HORMONE BINDING DOMAIN ENDS HERE -

NUCLEIC ACID ENCODING SITE SPECIFIC RECOMBINASE AND NUCLEAR RECEPTOR FUSION PROTEIN

SPECIFICATION

The present invention relates to the technical field of genetic manipulation, and more specifically, to the use of recombination-mediated DNA rearrangements and to the use of the regulatory potential of nuclear receptors.

The use of site-specific recombinases (SSRs) to induce defined rearrangements of DNA has been described in a variety of organisms (1–12). These reports describe the introduction of a DNA construct that contains SSR target sites. Subsequent exposure to the SSR enzyme activity resulted in the DNA rearrangement determined by the disposition of the target sites (see reference 13 for a recent review of SSRs). Three SSRs have been used in this manner to date; FLP recombinase from the 2 μ episome of *Saccharomyces cerevisiae* (1,2,5,6,9,10), CRE recombinase from the *Escherichia coli* phage P1 (3,4,8,11,12) and R recombinase from pSR1 of *Zygosaccharomyces rouxii* (7). Amongst other SSR systems relevant to the invention described here are those listed in references 13 and 14, and SSRs from *Kluyveromyces drosophilarium* (15), *Kluyveromyces waltii* (16), λ Int (17) and the Gin recombination system from phage Mu (18). The content of the above document is incorporated by reference.

For many applications in cells, organisms and cell-free in vitro systems, SSR induced DNA rearrangements must be regulated. Current implementation of the potential offered by SSRs is limited by the means available to regulate SSR activity. In experiments with cultured cells, unregulated SSRs have been used. For example, after introduction of SSR target sites into cells, recombination has been induced by subsequent introduction of either FLP recombinase by transfection of DNA (4,9) or injection of CRE recombinase protein (12). That is, the intended recombination event was regulated merely by the time of introduction of an appropriate macromolecule. Amongst other limitations, this precludes the creation and proliferation of homogeneous populations of cells that contain both the unrearranged target sites and the SSR and in which the recombination event can be induced after cell numbers have been expanded.

In experiments with transgenic animals, the issue of SSR regulation has been addressed by regulating the expression of an introduced SSR gene using the inducible heat-shock promoter in Drosophila (5) or a tissue-specific promoter in mice (11). Both approaches have limited applicability. Namely, heat-shock regulation of transgene expression is currently only useful in flies and no suitable counterpart is available for use in cell lines or vertebrates. Also, the use of a tissue-specific promoter to regulate transgene expression relies on the limited availability of suitable promoters and enhancers and the expression pattern achieved is confined to the times and places at which these tissue specific elements are active.

The problem underlying the present invention was to provide a regulated recombination system, wherein the disadvantages of the prior art are at least partially eliminated. More specifically, the problem was to provide a recombination system, wherein the recombination event can be induced independently from any tissue specific restrictions.

This patent application describes an invention that regulates SSR activity, rather than its expression. Thus any means of achieving and directing expression can be used, such as using ubiquitous or broadly active promoters and enhancers, as well as tissue specific or inducible promoters and enhancers.

One aspect of the present invention relates to a fusion protein, comprising a recombinase protein or a component of a recombinase complex, fused to part or all of a nuclear receptor, so that the amino acids that bind the ligand of said nuclear receptor are included, such that in cells or appropriate cell-free systems: (a) recombinase activity is inhibited in the absence of ligand binding to said ligand binding domain and (b) recombinase activity is induced or altered by binding of ligand to said ligand binding domain.

Preferably the recombinase activity is altered by binding of ligand to ligand binding domain by a factor of at least 10, more preferably of at least 20 and most preferably of at least 40.

The present invention resides in the regulation of SSR activity by fusing an SSR protein to the ligand binding domain (LBD) of a nuclear receptor. SSR-LBD fusion proteins comprise an amino acid sequence of SSRs physically attached to the amino acid sequence of an LBD of a nuclear receptor. That is, the invention is a fusion protein, comprising a recombinase protein, or a component of a recombinase complex, fused to the ligand binding domain of a nuclear receptor. Preferably, the recombinase protein or a component of a recombinase complex is fused to the nuclear receptor or ligand binding domain thereof by means of genetic fusion, i.e. the SSR-LBD protein is a linear genetic fusion encoded by a single nucleic acid. On the other hand, the present invention also encompasses SSR-LBD fusion proteins which are linked by different means, e.g. through a spacer molecule having reactive groups thereon, which are covalently bound to each protein domain.

Most simply, the attachment of the SSR and LBD components can be achieved by making a DNA construct that encodes for the amino acid sequence of the SSR-LBD fusion protein with the LBD encoding DNA placed in the same reading frame as the SSR encoding DNA, preferably either at the amino or carboxy termini of the SSR protein (19). More preferably, the nuclear receptor or ligand binding domain thereof is fused to the C-terminus of the recombinase protein or component of a recombinase complex. In an especially preferred embodiment of the present invention the nuclear receptor or ligand binding domain thereof is fused to the recombinase protein or component of a recombinase complex through a peptide linker which mainly consists of hydrophilic acids and preferably has a length of 4 to 20 amino acids.

SSR-LBD fusion proteins can coexist with target sites without recombination occurring since these proteins require ligand binding to the LBD for recombinase activity. In our experiments, recombinase activity of the SSR-LBD fusion protein, in the absence of the relevant ligand, is at least 200× less active than wild type recombinase activity. Upon presenting the SSR-LBD fusion proteins with the relevant ligand, recombinase activity is induced to more than 20% of wild type, that is, equal to or greater than 40× induction. This is the first description of post-transcriptional regulation of SSRs by any means. In particular, the invention permits the propagation of both the unrearranged target sites and the SSR-LBD in living systems. More specifically:

(a) cell lines can be established that carry both the unrearranged target sites and the SSR-LBD as a prerequisite for biochemical studies or introduction into organisms. The cell lines can be homogeneous and characterised before expansion to the required quantities and subsequent induction of recombination by administration of the relevant ligand, (b) recombination can be regulated in any experimentally manipulatable multicellular organism by administration of the relevant ligand. The SSR-LBD could be introduced to the organism either through the incorporation of cells or by direct means such as microinjection or in the genome of a viral based vector. Recombination can be induced after characterisation by administration of the relevant ligand.

The term "nuclear receptor", as used herein, refers to a molecule, preferably a protein molecule, which may be glycosylated or unglycosylated, having the abilities to bind ligand and to be incorporated into a nucleus of a cell. Specifically, the term nuclear receptor refers to those proteins that display functional or biochemical properties that are similar to the functional or biochemical properties displayed by the steroid hormone receptors with respect to ligand binding, for example, the dioxin receptor (Whitelaw, M. L., Göttlicher, M., Gustafsson, J. -A. and Poellinger, L., (1993) EMBO J. 12, 4169–4179). More specifically, the term nuclear receptor refers to those proteins that are related by their amino acid sequence to the LBDs of the steroid hormone receptors. The paper of Laudet et al. (1992) (Laudet, V., Hänni, C., Coll, J., Catzeflis, F. and Stehelin, D. (1992) EMBO J. 11, 1003–1013) describes an alignment of nuclear receptor amino acid sequences using standard methodologies. Included in the definition of nuclear receptors used here are also those proteins not listed in Laudet et al. but which can be included using the methods employed by Laudet et al. The term nuclear receptor also includes mutant derivatives of nuclear receptor amino acid sequences which retain sufficient relatedness to nuclear receptor amino acid sequences as to be identifiable as related using the methods employed by Laudet et al.

The nuclear receptor which is fused to the recombinase protein is preferably a hormone receptor, e.g. a receptor recognized by steroids, vitamins or related ligands. Examples of suitable nuclear receptors are listed in reference 20, which is hereby incorporated by reference. Preferably, the nuclear receptor is a steroid hormone receptor, more preferably, a glucocorticoid, estrogen, progesteron, or androgen receptor.

In the SSR-LBD fusion protein of the present invention, it is not required that the complete nuclear receptor is present; i.e. it is sufficient that the amino acids that bind the ligand are fused to the SSR.

Upon binding their relevant ligand, nuclear receptors become active, or altered, transcription factors. The cloning of cDNAs encoding members of the steroid receptor family of proteins revealed that they share amino acid sequence homology, in particular in the protein domain that binds ligand. The LBD can be separated from the rest of the protein and fused to other transcription factors conferring ligand regulation onto the resulting fusion proteins. For the glucocorticoid and estrogen receptors, the domain that binds ligand has been fused to other transcription factors and also to oncoproteins, rendering the fusion proteins dependent on the relevant ligand for activity (19,21–26). All characterised oncoproteins that have been experimentally regulated in this manner so far are also transcription factors. Transcription factors and oncoproteins are not enzymes in the classical sense and the regulation of their activities by steroids and LBDs described in references 19, 21–26, is essentially similar to the role that LBDs play in regulating steroid receptors. Prior attempts to extend the regulatory possibilities of the LBD fusion protein strategy beyond transcription factors and oncoproteins have yet to be reported. Attempts to regulate the enzyme activities of either β-galactosidase or dihydrofolate reductase by fusing them with the glucocorticoid LBD have been unsuccessful (D. Picard, public seminar given at EMBL, Heidelberg, Nov. 1991).

The present invention extends the regulatory possibilities of the LBD fusion protein strategy beyond the currently documented transference of ligand regulation from nuclear receptors to other transcription factors, to include an enzyme activity, namely a site specific recombinase. The term "site specific recombinase" refers to any protein component of any recombinant system that mediates DNA rearrangements in a specific DNA locus, including site specific recombinases of the integrase or resolvase/invertase classes (13; Abremski, K. E. and Hoess, R. H. (1992) Protein Engineering 5, 87–91; Khan, E., Mack, J. P. G., Katz, R. A., Kulkosky, J. and Skalka, A. M. (1991) Nucleic acids Res. 19, 851–860) and site-specific recombination mediated by intron-encoded endonucleases (Perrin, A., Buckle, M. and Dujon, B. (1993) EMBO J. 12, 2939–2947). Preferred recombinase proteins, which can be used in the fusion proteins according to the invention, are selected from the group consisting of: FLP recombinase, Cre recombinase, R recombinase from the *Zygosaccharomyces rouxii* plasmid PSR1, A recombinase from the *Kluyveromyces drosophilarium* plasmid pKD1, A recombinase from the *Kluyveromyces waltii* plasmid pKW1, any component of the λ Int recombination system, any component of the Gin recombination system, or variants thereof. The term "variant" in this context refers to proteins which are derived from the above proteins by deletion, substitution and/or addition of amino acids and which retain their some or all of the function inherent in the protein from which they are derived. Specifically, the variant could retain the ability to act as a recombinase, or it could retain protein/protein or protein/DNA interactions critical to the recombination reaction, or to the regulation of the recombination reaction.

In a preferred embodiment of the invention, FLP recombinase is fused to the LBD of the estrogen, glucocorticoid, progesterone or androgen receptors (20). Other preferred embodiments include fusing Cre recombinase or R recombinase, or SSRs from *Kluyveromyces drosophilarium* or *Kluyveromyces waltii,* to these LBDs. Another preferred embodiment involves regulating one or more components of an SSR complex to these LBDs, in particular, components of the λ Int or Gin recombination systems. The invention, in providing a means to regulate recombination, is however not limited to known recombinases and recombination complexes and is not limited to known nuclear receptor LBDs. Rather, the strategy of fusing recombinases, or components of recombination complexes, to LBDs of nuclear receptors is applicable to any fusion combination of these proteins which display the desired characteristics readily identifiable without undue experimentation on the part of a skilled person.

A further subject-matter of the present invention is a nucleic acid which encodes the fusion protein according to the present invention. Preferably, the nucleic acid is a DNA or RNA.

Still a further subject-matter of the present invention is a recombinant vector comprising at least one copy of the nucleic acid as defined above. This recombinant vector may be a eukaryotic vector, a viral vector, or a prokaryotic vector, or a vector which can be maintained in eukaryotic and prokaryotic host cells. The recombinant vector is obtainable by inserting a nucleic acid encoding a SSR-LBD fusion protein into a suitable starting vector. Specific examples of suitable starting vectors are given for example in Molecular Cloning. A Laboratory Manual, 2nd edition, J. Sambrook et al. (1989), Cold Spring Harbor Laboratory Press, chapters 1, 2, 3, 4, 16 and 17.

The vector of the present invention may be an extra-chromosomal vector or a vector which integrates into the genome of the host cell. Extra-chromosomal vectors, e.g. circular plasmids are especially preferred. An example of a plasmid vector is the plasmid pHFE1 comprising a nucleic acid encoding a fusion of the FLP recombinase and the ligand binding domain of the estrogen receptor. The plasmid PHFE1 has been deposited at the Deutsche Sammlung von Mikroorganismen und Zellkulturen GmbH (DSM), Mascheroder Weg 1b, D-38124 Braunschweig on Jun. 25, 1994 under the accession number DSM 9265 according to the requirements of the Budapest Treaty.

Still a further subject-matter of the present invention is a cell containing a nucleic acid or a recombinant vector as defined above. Preferably, the cell is stably transformed with the nucleic acid or the vector. Suitable cells are eukaryotic or prokaryotic cells. Examples of prokaryotic cells are gram-negative bacterial cells, especially E. coli cells. Examples of eukaryotic cells are mammalian cells, yeasts and trypanosomes.

The invention separates the function of ligand binding from the functions of transcription factors, coupling ligand binding to recombinase activity. Thereby, the binding of ligand can be assessed by any means that measures recombinase activity. Thus, further embodiments of the invention include methods for determining the binding of ligand to the LED of a nuclear receptor, comprising the steps of:

(i) the introduction of the SSR-LBD fusion protein or the nucleic acid coding therefor into cells, or appropriate cell-free systems, that contain the DNA target sites for the SSR;

(ii) administering the ligand or a mixture suspected to contain a ligand or ligands to be evaluated; if the ligand is not already present in the system; (iii) detecting the recombinase activity, if any, of the SSR-LBD by detecting, directly or indirectly, recombination or changes in the recombination rate between the DNA target sites.

The introduction of SSR-LBD fusion proteins into cells may be accomplished by transforming the cells with appropriate vectors containing a nucleic acid coding for the SSR-LBD fusion protein. The administration of the ligand to be evaluated is not necessary in systems which already contain the ligand and in which the ligand-concentration is determined by detecting recombination between DNA target sites.

Particularly preferred embodiments include:

(a) direct measurements of the physical arrangement of the target sites using techniques such as gel electrophoresis of DNA molecules, Southern blotting or polymerase chain reaction.

(b) indirect measurements by assessing the properties encoded by the DNA regions carrying the target sites before or after recombination. For example, recombination could excise an antibiotic resistance gene from the genome of the host and thus recombination can be measured as sensitivity to the antibiotic.

(c) the measurement of intracellular ligand concentrations by evaluating recombination between the DNA target sites resident in the cells that also carry the SSR-LBD fusion proteins.

(d) the evaluation of ligand binding to an LBD without the need to use radiolabelled ligand derivatives or without reliance on the transcription factor properties of the corresponding nuclear receptor.

(e) evaluating the effect of mutations in the LBD on ligand binding. Since SSR-LBD recombination requires ligand, mutations in the LBD that decrease ligand binding can be ascertained. Alternatively, mutations that improve binding of a different ligand can be selected. For example, ligand-dependent recombination could rearrange the DNA, so that an antibiotic resistance gene is expressed. Cells with the rearranged DNA will grow under the appropriate antibiotic selection, cells with unrearranged DNA will not. Specifically this describes a method for determining the effect of mutations in the LBD of a nuclear receptor on its ability to bind ligand, comprising the steps of (a) introducing mutations into the LBD of the SSR-LBD fusion protein, and (b) following steps (i) to (iii) above.

The invention also encompasses a method for regulating the recombination of DNA target sites, comprising the steps of:

(a) providing cells or appropriate cell-free systems that contain DNA target sites for a site-specific recombinase, (b) contacting the DNA target sites with a fusion protein according to the present invention, which contacting may be accomplished by direct introduction of the protein or by transformation of a cell with the nucleic acid encoding the protein and expressing the nucleic acid to produce the protein, (c) effecting a recombination of said DNA target sites by contacting the fusion protein with a ligand for the nuclear receptor component of the fusion protein, e.g. by adding the ligand to the system at a predetermined time, or by effecting production of the ligand in the system at a predetermined time.

DESCRIPTION OF THE FIGURES

FIG. 1A depicts the plasmid, pNEOβGAL (thin line), integrated into the genome of 293 cells (thick line). FLP recombinase target sites (FRTs) are depicted as broad arrows and the neomycin resistance gene lies between the two FRTs. Upon estradiol administration, the DNA between the FRTs is excised, leaving one FRT in the genome and one on the excised circular DNA. The probe used for the Southern blot of FIG. 2 is also depicted.

FIG. 2 shows a Southern blot of a timecourse of recombination occurring in the cell line P1.4. At the times indicated after estradiol, or ethanol only, administration in the upper part of the figure, cells were lysed, DNA purified, restricted with NdeI, run on a 1.25% agarose gel and blotted to Biodyne B membranes by standard methodologies. The membrane was hybridized with the radioactively labelled probe depicted in FIG. 1A. The upper band shows the unrecombined integrated DNA and the lower the recombined band. Estradiol was dissolved in ethanol and the extreme right hand lane shows cells treated with the equivalent amount of ethanol, without estradiol, for 51 hours.

The following examples are offered by way of illustration and is not intended to limit the invention in any manner.

EXAMPLE 1

Construction of Plasmid Containing a SSR-LBD-fusion Gene

Figure 1A:
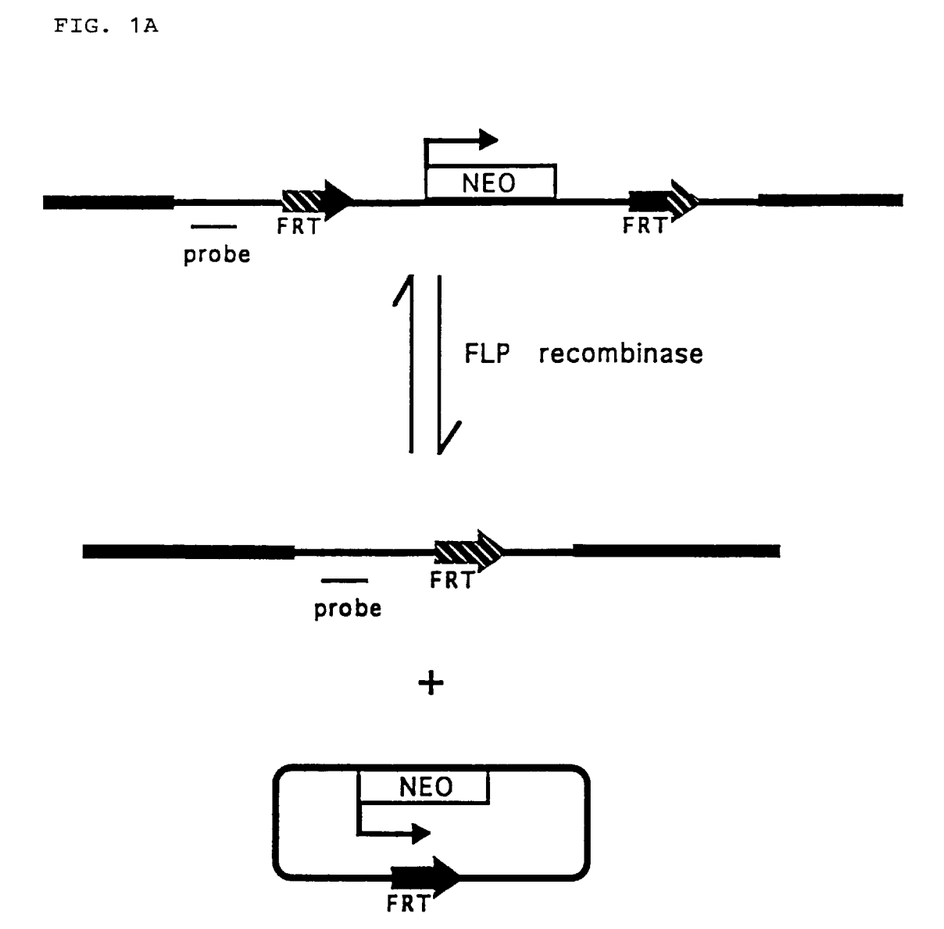
Figure 1B:
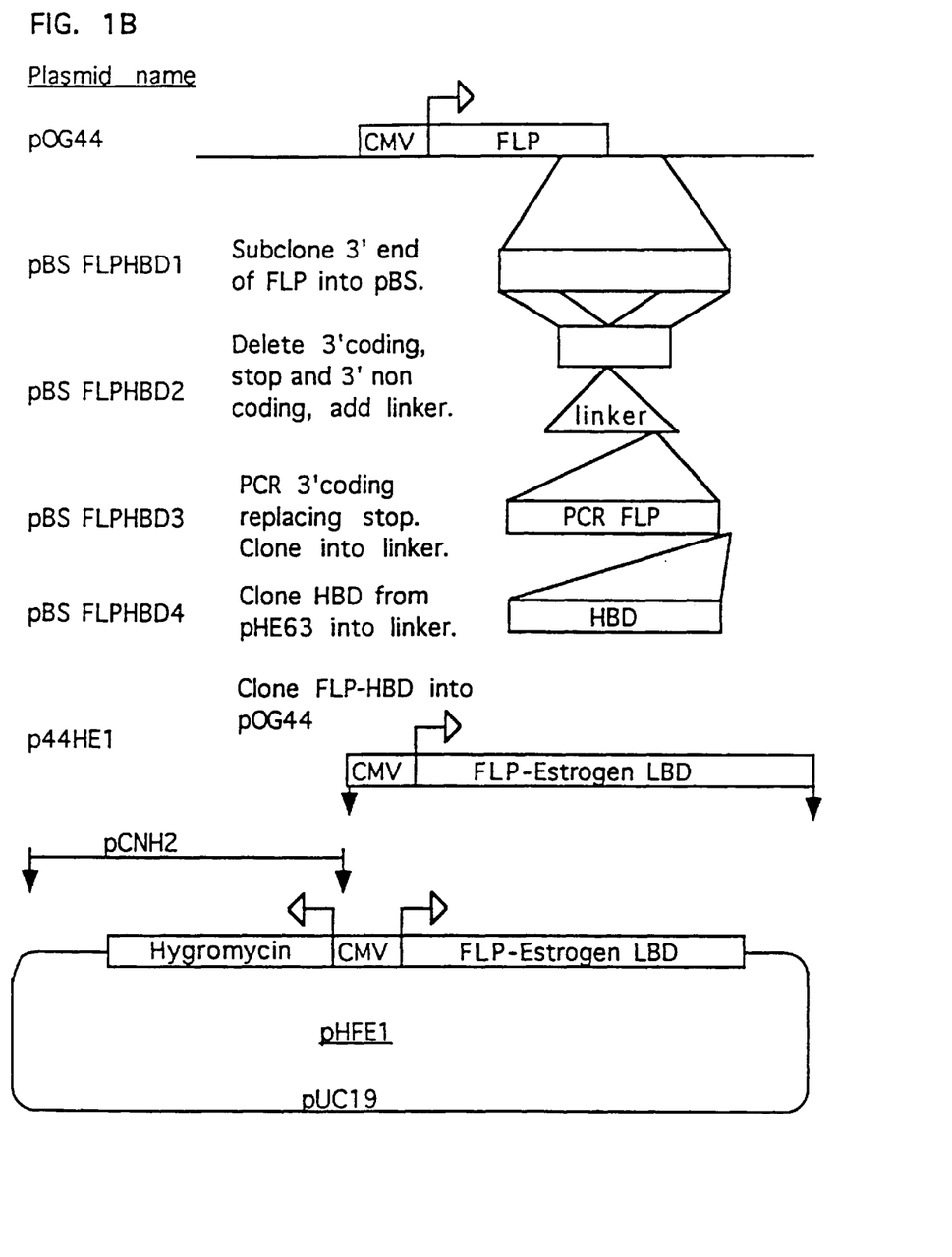
FIG. 1B depicts the steps involved in the creation of plasmid pHFE1.

The experiment involves two plasmids, one of which is the target for recombination, and the other is the recombinase expression plasmid. As the target plasmid, pNEOβGAL (9) was employed. pNEOβGAL contains two FLP recombinase target sites (FRT) surrounding a gene encoding neomycin resistance (FIG. 1a). The expression plasmid, pHFE 1, carries two genes, one encoding an FLP recombinase-estrogen receptor LBD fusion protein and the other encoding hygromycin resistance (FIG. 1b). The plasmid was constructed by standard cloning procedures using pBluescribe (Stratagene), pOG 44 (9), pHE63 (22) and pCNH2 (27). The stop codon of the FLP recombinase coding region present in pOG44 was mutated by oligonucleotide replacement to introduce BamH1, BsiW1 and EcoR1 sites and continue the open reading frame. The BamHI site in the estrogen receptor encoded by pHE63 was used to join the coding regions of FLP recombinase and estrogen receptor LBD. All of the estrogen receptor coding region carboxy to the BamHI site is present in the plasmid, including its stop codon.

EXAMPLE 2

Figure 2:
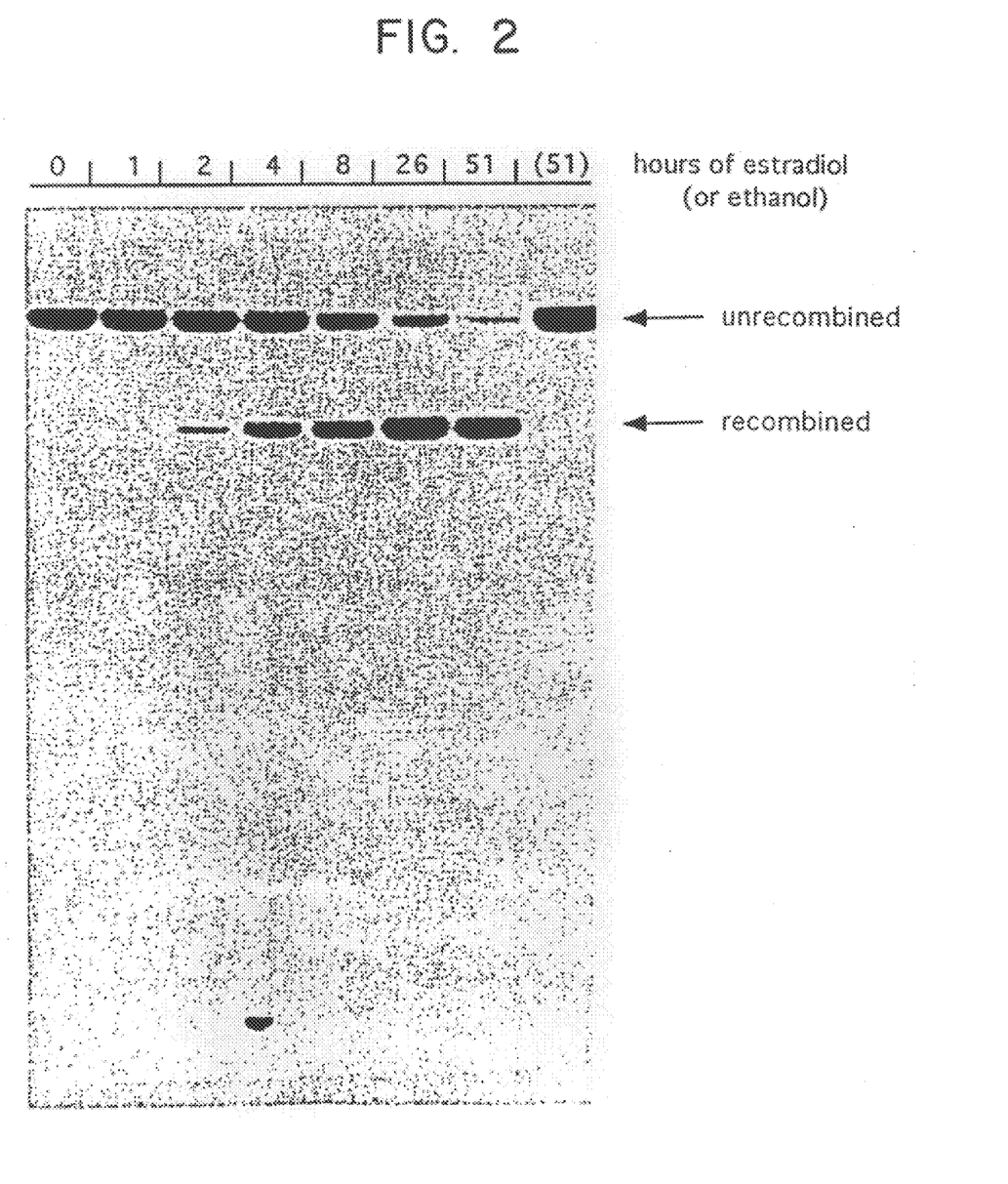
Figure 3:
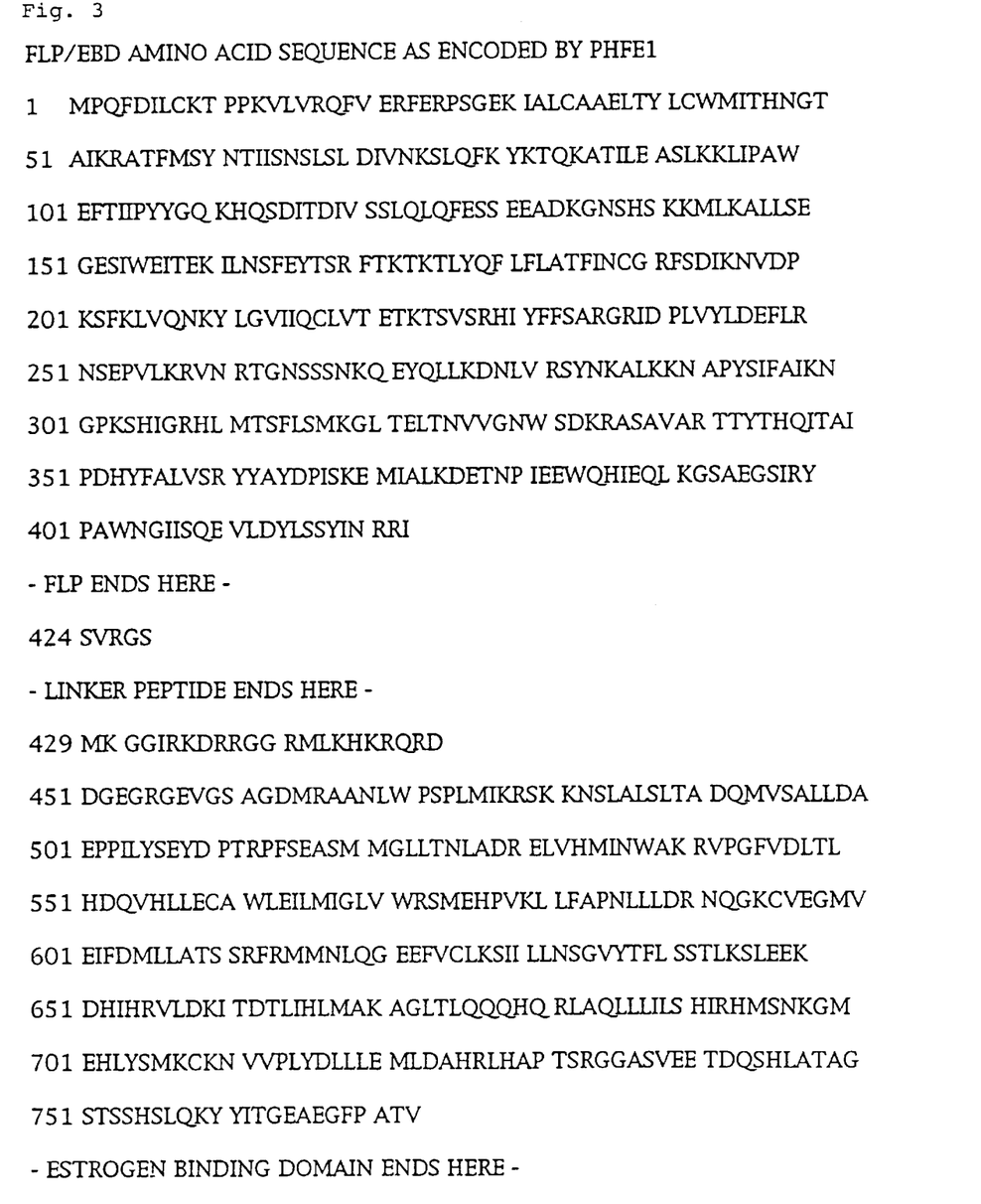
FIG. 3 shows the complete amino acid sequence of the SSR-LBD-fusion polypeptide encoded by the plasmid pHFE1 [SEQ ID NO: 1]. The FLP recombinase domain is located from amino acid 1–423. The linker peptide is located from amino acid 424–428. The estrogen binding domain is located from amino acid 429–773.
Figure 4:
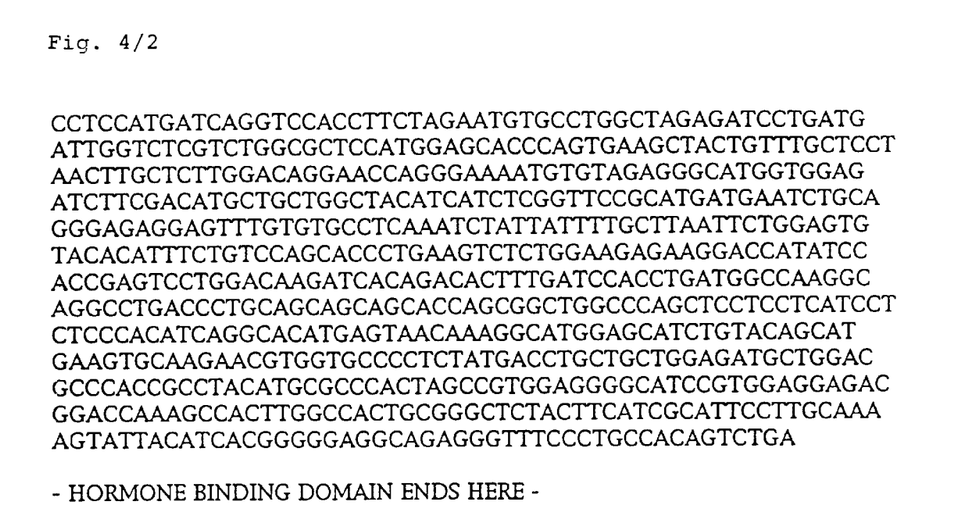
FIG. 4 shows the nucleic acid sequence coding for the SSR-LBD fusion polypeptide of FIG. 3 [SEQ ID NO: 2]. The parts coding for the FLP recombinase domain, the linker peptide and the estrogen binding domain, respectively, are specified.

Regulation of Site Specific Recombination pNEOβGAL was introduced into 293 human embryonal kidney cells by electroporation ($5 \times 10^6$ cells in 500 μl phosphate-buffered saline with 5 μg of ApaI linearised plasmid; 300 V at 125 μF in a 1 ml cuvette using a Bio-Rad Gene Pulser) and selection for neomycin resistance (G418, 0.4 mg/ml). Single colonies of resistant cells were cloned and characterised for incorporation of target plasmid DNA by Southern blotting. A clone, P1, showing integration of a single copy of target plasmid DNA was selected and transfected, using the calcium phosphate procedure, with the second plasmid, PHFE 1 (1 μg of XmnI linearised pHFE 1 was precipitated by the standard calcium phosphate method onto $10^7$ P1 cells which were cultured in DMEM without phenol red, 10% charcoal stripped fetal calf serum). Four clones resistant to both neomycin and hygromycin (0.4 mg/ml G418, 0.4 mg/ml hygromycin B) were isolated and the dependance of recombination on estradiol administration was observed in all four. For clone P1.4, a time course of recombination in the presence of $10^{-6}$ M estradiol is shown (FIG. 2).

REFERENCES

1. Falco, S. C., Li. Y., Broach, J. R. and Botstein, D. (1982) Cell 29, 573–584.
2. Cox, M. M. (1983) Proc. Natl. Acad. Sci. USA 80, 4223–4227.
3. Sauer, B. (1987) Mol. Cell. Biol. 7, 2087–2096.
4. Sauer, B. and Henderson, N. (1989) Nucleic Acids Res. 17, 147–161.
5. Golic, K. G. and Lindquist, S. (1989) Cell 59, 499–509.
6. Cregg, J. M. and Madden, K. R. (1989) Mol. Gen. Genet. 219, 320–323.
7. Matsuzaki, H. et al. (1990) J. Bacteriol. 172, 610–618.
8. Odell, J., Caimi, P., Sauer, B. and Russell, S. (1990) Mol. Gen. Genet. 223, 369–378.
9. O'Gorman, S., Fox, D. T. and Wahl, G. M. (1991) Science 251, 1351–1355.
10. Konsolaki, M. et al (1992) New Biologist 4, 551–557.
11. Lakso, M. et al (1992) Proc. Natl. Acad. Sci. USA 89, 6232–6236.
12. Baubonis, W. and Sauer, B. (1993) Nucleic Acids Res. 21, 2025–2029.
13. Stark, W. M. et al. (1992) Trends Genet. 8. 432–439.
14. Utatsu, I. et al (1987) J. Bacteriol. 169, 5537–5545.
15. Chen, X. J. et al (1986) Nucleic Acids Res. 314, 4471–4481.
16. Chen, Y. J. et al (1992) J. Gen. Microbiol. 138, 337–345.
17. Landy, A. (1989) Annu. Rev. Biochem. 58, 913–949.
18. Klippel, A. et al (1993) EMBO J. 12, 1047–1057.
19. Webster, N. J. G. et al (1988) Cell 54, 194–207
20. Beato, M. (1989) Cell 56, 335–344.
21. Kumar, V. et al (1987) Cell 51, 941–951.
22. Picard, D. Salser, S. J. and Yamamoto, K. R. (1988) Cell 54, 1073–1080.
23. Eilers, M., Picard, D., Yamamoto, K. R. and Bishop, M. (1989) Nature 340, 66–68.
24. Superti-Furga, G. et al (1991) Proc. Natl. Acad. Sci. USA 88, 5114–5118.
25. Burk, O. and Klempenauer, K. -H. (1991) EMBO J. 10, 3713–3719.
26. Boehmelt, G. et al (1992) EMBO J. 11, 4641–4652.
27. Schmidt, E. et al (1990) Mol. Cell. Biol. 10, 4406–4411.

I claim:

1. A fusion protein, comprising (1) a site specific recombinase protein and (2) the ligand binding domain of a nuclear receptor which is attached at the C- or N-terminus of said site specific recombinase protein, such that, in a cell or cell-free system containing DNA target sites which are specifically recognized by said site specific recombinase protein:

(a) site specific recombinase activity of said fusion protein in relation to the DNA target sites is inhibited in the absence of ligand binding to said ligand binding domain, and (b) inhibition of said site specific recombinase activity of said fusion protein in relation to the DNA target sites is relieved by binding of ligand to said ligand binding domain.

2. The fusion protein of claim 1, wherein the site specific recombinase protein is a specific DNA binding component of a site specific recombinase complex.

3. The fusion protein of claim 1, wherein the site specific recombinase protein is a recombinase enzyme component of a site specific recombinase complex.

4. The fusion protein of claim 1, wherein the nuclear receptor is selected from the group consisting of a vertebrate glucocorticoid, estrogen, progesterone and androgen receptor.

5. The fusion protein of claim 1, wherein the site specific recombinase protein is selected from the group consisting of FLP recombinase, Cre recombinase, R recombinase from the *Zygosaccharomyces rouxii* plasmid pSR1, A recombinase from the *Kluyveromyces drosophilarium* plasmid pKD1, A recombinase from the *Kluyveromyces waltii* plasmid pKW1, the specific DNA binding component of the λ Int recombinase complex and the enzyme component of the λ Int recombinase complex.

6. A nucleic acid which encodes the fusion protein of claim 1.

7. A recombinant vector, comprising at least one copy of the nucleic acid of claim 6.

8. The plasmid pHFE1 (DSM 9265).

9. A cell containing the nucleic acid of claim 6.

10. A cell containing the recombinant vector of claim 7.

11. A method for determining the binding of a ligand to be evaluated to the ligand binding domain of a nuclear receptor, comprising
   (a) introducing the fusion protein of claim 1 into a cell or appropriate cell-free system containing DNA target sites which are specifically recognized by the site specific recombinase protein,
   (b) if the cell or cell-free system does not already contain the ligand to be evaluated, introducing the ligand or a sample suspected of containing the ligand into the cell or cell-free system; and
   (c) determining the binding of the ligand to the ligand binding domain by detecting the presence of or change in recombinase activity of the fusion protein in relation to the DNA target sites.

12. The method of claim 11, wherein the ligand binding domain of the fusion protein is a mutation of a wild-type ligand binding domain.

13. A method for determining the binding of a ligand to be evaluated to the ligand binding domain of a nuclear receptor, comprising
   (a) introducing the nucleic acid of claim 6 into a cell or appropriate cell-free system containing DNA target sites which are specifically recognized by the site specific recombinase protein and expressing the nucleic acid to produce the fusion protein;
   (b) if the cell or cell-free system does not already contain the ligand to be evaluated, introducing the ligand or a sample suspected of containing the ligand into the cell or cell-free system; and
   (c) determining the binding of the ligand to the ligand binding domain by detecting the presence of or change in recombinase activity of the fusion protein in relation to the DNA target sites.

14. The method of claim 13, wherein the ligand binding domain of the fusion protein is mutated relative to the wild-type ligand binding domain.

15. A method for regulating the recombination of DNA target sites, comprising
   (a) providing a cell or appropriate cell-free system containing DNA target sites which are specifically recognized by the site specific recombinase protein;
   (b) contacting the fusion protein of claim 1 with a ligand for the ligand binding domain of the fusion protein and contacting the DNA target sites with the fusion protein; and
   (c) effecting recombination of the DNA target sites by the site specific recombinase protein.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 773 amino acids
      (B) TYPE: amino acid
      (D) TOPOLOGY: linear (ii) MOLECULE TYPE: protein (ix) FEATURE:
      (A) NAME/KEY: misc_feature
      (B) LOCATION: (1-423)
      (D) OTHER INFORMATION: /note= "FLP recombinase domain."

```
    (ix) FEATURE:
          (A) NAME/KEY: misc_feature
          (B) LOCATION: (424-428)
          (D) OTHER INFORMATION: /note= "Linker peptide."

(ix) FEATURE:
          (A) NAME/KEY: misc_feature
          (B) LOCATION: (429-773)
          (D) OTHER INFORMATION: /note= "Estrogen binding domain."

(xi) SEQUENCE DESCRIPTION: SEQ ID NO: 1:

Met Pro Gln Phe Asp Ile Leu Cys Lys Thr Pro Pro Lys Val Leu Val
 1               5                  10                  15

Arg Gln Phe Val Glu Arg Phe Glu Arg Pro Ser Gly Glu Lys Ile Ala
                 20                  25                  30

Leu Cys Ala Ala Glu Leu Thr Tyr Leu Cys Trp Met Ile Thr His Asn
         35                  40                  45

Gly Thr Ala Ile Lys Arg Ala Thr Phe Met Ser Tyr Asn Thr Ile Ile
     50                  55                  60

Ser Asn Ser Leu Ser Ser Asp Ile Val Asn Lys Ser Leu Gln Phe Lys
 65                  70                  75                  80

Tyr Lys Thr Gln Lys Ala Thr Ile Leu Glu Ala Ser Leu Lys Lys Leu
                 85                  90                  95

Ile Pro Ala Trp Glu Phe Thr Ile Ile Pro Tyr Tyr Gly Gln Lys His
                100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
                180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
                260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
                340                 345                 350
```

```
His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile Ser Val Arg Gly Ser Met Lys Gly Gly
            420                 425                 430

Ile Arg Lys Asp Arg Arg Gly Gly Arg Met Leu Lys His Lys Arg Gln
        435                 440                 445

Arg Asp Asp Gly Glu Gly Arg Gly Val Gly Ser Ala Gly Asp Met
450                 455                 460

Arg Ala Ala Asn Leu Trp Pro Ser Pro Leu Met Ile Lys Arg Ser Lys
465                 470                 475                 480

Lys Asn Ser Leu Ala Leu Ser Leu Thr Ala Asp Gln Met Val Ser Ala
                485                 490                 495

Leu Leu Asp Ala Glu Pro Pro Ile Leu Tyr Ser Glu Tyr Asp Pro Thr
                500                 505                 510

Arg Pro Phe Ser Glu Ala Ser Met Met Gly Leu Leu Thr Asn Leu Ala
        515                 520                 525

Asp Arg Glu Leu Val His Met Ile Asn Trp Ala Lys Arg Val Pro Gly
    530                 535                 540

Phe Val Asp Leu Thr Leu His Asp Gln Val His Leu Leu Glu Cys Ala
545                 550                 555                 560

Trp Leu Glu Ile Leu Met Ile Gly Leu Val Trp Arg Ser Met Glu His
                565                 570                 575

Pro Val Lys Leu Leu Phe Ala Pro Asn Leu Leu Leu Asp Arg Asn Gln
            580                 585                 590

Gly Lys Cys Val Glu Gly Met Val Glu Ile Phe Asp Met Leu Leu Ala
        595                 600                 605

Thr Ser Ser Arg Phe Arg Met Met Asn Leu Gln Gly Glu Glu Phe Val
    610                 615                 620

Cys Leu Lys Ser Ile Ile Leu Leu Asn Ser Gly Val Tyr Thr Phe Leu
625                 630                 635                 640

Ser Ser Thr Leu Lys Ser Leu Glu Glu Lys Asp His Ile His Arg Val
                645                 650                 655

Leu Asp Lys Ile Thr Asp Thr Leu Ile His Leu Met Ala Lys Ala Gly
            660                 665                 670

Leu Thr Leu Gln Gln Gln His Gln Arg Leu Ala Gln Leu Leu Leu Ile
        675                 680                 685

Leu Ser His Ile Arg His Met Ser Asn Lys Gly Met Glu His Leu Tyr
    690                 695                 700

Ser Met Lys Cys Lys Asn Val Val Pro Leu Tyr Asp Leu Leu Leu Glu
705                 710                 715                 720

Met Leu Asp Ala His Arg Leu His Ala Pro Thr Ser Arg Gly Gly Ala
                725                 730                 735

Ser Val Glu Glu Thr Asp Gln Ser His Leu Ala Thr Ala Gly Ser Thr
            740                 745                 750

Ser Ser His Ser Leu Gln Lys Tyr Tyr Ile Thr Gly Glu Ala Glu Gly
        755                 760                 765

Phe Pro Ala Thr Val
```

(2) INFORMATION FOR SEQ ID NO: 2:

(i) SEQUENCE CHARACTERISTICS:
        (A) LENGTH: 2322 base pairs
        (B) TYPE: nucleic acid
        (C) STRANDEDNESS: single
        (D) TOPOLOGY: linear     (ix) FEATURE:
        (A) NAME/KEY: misc_feature
        (B) LOCATION: (1-1269)
        (D) OTHER INFORMATION: /note= "FLP recombinase domain."

(ix) FEATURE:
        (A) NAME/KEY: misc_feature
        (B) LOCATION: (1270-1284)
        (D) OTHER INFORMATION: /note= "Linker peptide."

(ix) FEATURE:
        (A) NAME/KEY: misc_feature
        (B) LOCATION: (1285-2322)
        (D) OTHER INFORMATION: /note= "Estrogen binding domain."

(xi) SEQUENCE DESCRIPTION: SEQ ID NO: 2:

```
ATG CCA CAA TTT GAT ATA TTA TGT AAA ACA CCA CCT AAG GTG CTT GTT        48
Met Pro Gln Phe Asp Ile Leu Cys Lys Thr Pro Pro Lys Val Leu Val
 1               5                  10                  15

CGT CAG TTT GTG GAA AGG TTT GAA AGA CCT TCA GGT GAG AAA ATA GCA        96
Arg Gln Phe Val Glu Arg Phe Glu Arg Pro Ser Gly Glu Lys Ile Ala
                20                  25                  30

TTA TGT GCT GCT GAA CTA ACC TAT TTA TGT TGG ATG ATT ACA CAT AAC       144
Leu Cys Ala Ala Glu Leu Thr Tyr Leu Cys Trp Met Ile Thr His Asn
            35                  40                  45

GGA ACA GCA ATC AAG AGA GCC ACA TTC ATG AGC TAT AAT ACT ATC ATA       192
Gly Thr Ala Ile Lys Arg Ala Thr Phe Met Ser Tyr Asn Thr Ile Ile
        50                  55                  60

AGC AAT TCG CTG AGT TCC GAT ATT GTC AAC AAG TCA CTG CAG TTT AAA       240
Ser Asn Ser Leu Ser Ser Asp Ile Val Asn Lys Ser Leu Gln Phe Lys
 65                  70                  75                  80

TAC AAG ACG CAA AAA GCA ACA ATT CTG GAA GCC TCA TTA AAG AAA TTG       288
Tyr Lys Thr Gln Lys Ala Thr Ile Leu Glu Ala Ser Leu Lys Lys Leu
                85                  90                  95

ATT CCT GCT TGG GAA TTT ACA ATT ATT CCT TAC TAT GGA CAA AAA CAT       336
Ile Pro Ala Trp Glu Phe Thr Ile Ile Pro Tyr Tyr Gly Gln Lys His
                100                 105                 110

CAA TCT GAT ATC ACT GAT ATT GTA AGT AGT TTG CAA TTA CAG TTC GAA       384
Gln Ser Asp Ile Thr Asp Ile Val Ser Ser Leu Gln Leu Gln Phe Glu
            115                 120                 125

TCA TCG GAA GAA GCA GAT AAG GGA AAT AGC CAC AGT AAA AAA ATG CTT       432
Ser Ser Glu Glu Ala Asp Lys Gly Asn Ser His Ser Lys Lys Met Leu
        130                 135                 140

AAA GCA CTT CTA AGT GAG GGT GAA AGC ATC TGG GAG ATC ACT GAG AAA       480
Lys Ala Leu Leu Ser Glu Gly Glu Ser Ile Trp Glu Ile Thr Glu Lys
145                 150                 155                 160

ATA CTA AAT TCG TTT GAG TAT ACT TCG AGA TTT ACA AAA ACA AAA ACT       528
Ile Leu Asn Ser Phe Glu Tyr Thr Ser Arg Phe Thr Lys Thr Lys Thr
                165                 170                 175

TTA TAC CAA TTC CTC TTC CTA GCT ACT TTC ATC AAT TGT GGA AGA TTC       576
Leu Tyr Gln Phe Leu Phe Leu Ala Thr Phe Ile Asn Cys Gly Arg Phe
                180                 185                 190

AGC GAT ATT AAG AAC GTT GAT CCG AAA TCA TTT AAA TTA GTC CAA AAT       624
Ser Asp Ile Lys Asn Val Asp Pro Lys Ser Phe Lys Leu Val Gln Asn
            195                 200                 205
```

```
                                          -continued

AAG TAT CTG GGA GTA ATA ATC CAG TGT TTA GTG ACA GAG ACA AAG ACA       672
Lys Tyr Leu Gly Val Ile Ile Gln Cys Leu Val Thr Glu Thr Lys Thr
            210                 215                 220

AGC GTT AGT AGG CAC ATA TAC TTC TTT AGC GCA AGG GGT AGG ATC GAT       720
Ser Val Ser Arg His Ile Tyr Phe Phe Ser Ala Arg Gly Arg Ile Asp
225                 230                 235                 240

CCA CTT GTA TAT TTG GAT GAA TTT TTG AGG AAT TCT GAA CCA GTC CTA       768
Pro Leu Val Tyr Leu Asp Glu Phe Leu Arg Asn Ser Glu Pro Val Leu
                245                 250                 255

AAA CGA GTA AAT AGG ACC GGC AAT TCT TCA AGC AAC AAG CAG GAA TAC       816
Lys Arg Val Asn Arg Thr Gly Asn Ser Ser Ser Asn Lys Gln Glu Tyr
            260                 265                 270

CAA TTA TTA AAA GAT AAC TTA GTC AGA TCG TAC AAC AAA GCT TTG AAG       864
Gln Leu Leu Lys Asp Asn Leu Val Arg Ser Tyr Asn Lys Ala Leu Lys
            275                 280                 285

AAA AAT GCG CCT TAT TCA ATC TTT GCT ATA AAA AAT GGC CCA AAA TCT       912
Lys Asn Ala Pro Tyr Ser Ile Phe Ala Ile Lys Asn Gly Pro Lys Ser
290                 295                 300

CAC ATT GGA AGA CAT TTG ATG ACC TCA TTT CTT TCA ATG AAG GGC CTA       960
His Ile Gly Arg His Leu Met Thr Ser Phe Leu Ser Met Lys Gly Leu
305                 310                 315                 320

ACG GAG TTG ACT AAT GTT GTG GGA AAT TGG AGC GAT AAG CGT GCT TCT      1008
Thr Glu Leu Thr Asn Val Val Gly Asn Trp Ser Asp Lys Arg Ala Ser
                325                 330                 335

GCC GTG GCC AGG ACA ACG TAT ACT CAT CAG ATA ACA GCA ATA CCT GAT      1056
Ala Val Ala Arg Thr Thr Tyr Thr His Gln Ile Thr Ala Ile Pro Asp
            340                 345                 350

CAC TAC TTC GCA CTA GTT TCT CGG TAC TAT GCA TAT GAT CCA ATA TCA      1104
His Tyr Phe Ala Leu Val Ser Arg Tyr Tyr Ala Tyr Asp Pro Ile Ser
            355                 360                 365

AAG GAA ATG ATA GCA TTG AAG GAT GAG ACT AAT CCA ATT GAG GAG TGG      1152
Lys Glu Met Ile Ala Leu Lys Asp Glu Thr Asn Pro Ile Glu Glu Trp
370                 375                 380

CAG CAT ATA GAA CAG CTA AAG GGT AGT GCT GAA GGA AGC ATA CGA TAC      1200
Gln His Ile Glu Gln Leu Lys Gly Ser Ala Glu Gly Ser Ile Arg Tyr
385                 390                 395                 400

CCC GCA TGG AAT GGG ATA ATA TCA CAG GAG GTA CTA GAC TAC CTT TCA      1248
Pro Ala Trp Asn Gly Ile Ile Ser Gln Glu Val Leu Asp Tyr Leu Ser
                405                 410                 415

TCC TAC ATA AAT AGA CGC ATA TCC GTA CGC GGA TCC ATG AAA GGT GGG      1296
Ser Tyr Ile Asn Arg Arg Ile Ser Val Arg Gly Ser Met Lys Gly Gly
            420                 425                 430

ATA CGA AAA GAC CGA AGA GGA GGG AGA ATG TTG AAA CAC AAG CGC CAG      1344
Ile Arg Lys Asp Arg Arg Gly Gly Arg Met Leu Lys His Lys Arg Gln
            435                 440                 445

AGA GAT GAT GGG GAG GGC AGG GGT GAA GTG GGG TCT GCT GGA GAC ATG      1392
Arg Asp Asp Gly Glu Gly Arg Gly Glu Val Gly Ser Ala Gly Asp Met
450                 455                 460

AGA GCT GCC AAC CTT TGG CCA AGC CCG CTC ATG ATC AAA CGC TCT AAG      1440
Arg Ala Ala Asn Leu Trp Pro Ser Pro Leu Met Ile Lys Arg Ser Lys
465                 470                 475                 480

AAG AAC AGC CTG GCC TTG TCC CTG ACG GCC GAC CAG ATG GTC AGT GCC      1488
Lys Asn Ser Leu Ala Leu Ser Leu Thr Ala Asp Gln Met Val Ser Ala
                485                 490                 495

TTG TTG GAT GCT GAG CCC CCC ATA CTC TAT TCC GAG TAT GAT CCT ACC      1536
Leu Leu Asp Ala Glu Pro Pro Ile Leu Tyr Ser Glu Tyr Asp Pro Thr
            500                 505                 510

AGA CCC TTC AGT GAA GCT TCG ATG ATG GGC TTA CTG ACC AAC CTG GCA      1584
Arg Pro Phe Ser Glu Ala Ser Met Met Gly Leu Leu Thr Asn Leu Ala
```

```
                515                    520                    525
GAC AGG GAG CTG GTT CAC ATG ATC AAC TGG GCG AAG AGG GTG CCA GGC      1632
Asp Arg Glu Leu Val His Met Ile Asn Trp Ala Lys Arg Val Pro Gly
    530                    535                    540

TTT GTG GAT TTG ACC CTC CAT GAT CAG GTC CAC CTT CTA GAA TGT GCC      1680
Phe Val Asp Leu Thr Leu His Asp Gln Val His Leu Leu Glu Cys Ala
545                    550                    555                560

TGG CTA GAG ATC CTG ATG ATT GGT CTC GTC TGG CGC TCC ATG GAG CAC      1728
Trp Leu Glu Ile Leu Met Ile Gly Leu Val Trp Arg Ser Met Glu His
                565                    570                    575

CCA GTG AAG CTA CTG TTT GCT CCT AAC TTG CTC TTG GAC AGG AAC CAG      1776
Pro Val Lys Leu Leu Phe Ala Pro Asn Leu Leu Leu Asp Arg Asn Gln
            580                    585                    590

GGA AAA TGT GTA GAG GGC ATG GTG GAG ATC TTC GAC ATG CTG CTG GCT      1824
Gly Lys Cys Val Glu Gly Met Val Glu Ile Phe Asp Met Leu Leu Ala
        595                    600                    605

ACA TCA TCT CGG TTC CGC ATG ATG AAT CTG CAG GGA GAG GAG TTT GTG      1872
Thr Ser Ser Arg Phe Arg Met Met Asn Leu Gln Gly Glu Glu Phe Val
    610                    615                    620

TGC CTC AAA TCT ATT ATT TTG CTT AAT TCT GGA GTG TAC ACA TTT CTG      1920
Cys Leu Lys Ser Ile Ile Leu Leu Asn Ser Gly Val Tyr Thr Phe Leu
625                    630                    635                640

TCC AGC ACC CTG AAG TCT CTG GAA GAG AAG GAC CAT ATC CAC CGA GTC      1968
Ser Ser Thr Leu Lys Ser Leu Glu Glu Lys Asp His Ile His Arg Val
                645                    650                    655

CTG GAC AAG ATC ACA GAC ACT TTG ATC CAC CTG ATG GCC AAG GCA GGC      2016
Leu Asp Lys Ile Thr Asp Thr Leu Ile His Leu Met Ala Lys Ala Gly
            660                    665                    670

CTG ACC CTG CAG CAG CAG CAC CAG CGG CTG GCC CAG CTC CTC CTC ATC      2064
Leu Thr Leu Gln Gln Gln His Gln Arg Leu Ala Gln Leu Leu Leu Ile
        675                    680                    685

CTC TCC CAC ATC AGG CAC ATG AGT AAC AAA GGC ATG GAG CAT CTG TAC      2112
Leu Ser His Ile Arg His Met Ser Asn Lys Gly Met Glu His Leu Tyr
    690                    695                    700

AGC ATG AAG TGC AAG AAC GTG GTG CCC CTC TAT GAC CTG CTG CTG GAG      2160
Ser Met Lys Cys Lys Asn Val Val Pro Leu Tyr Asp Leu Leu Leu Glu
705                    710                    715                720

ATG CTG GAC GCC CAC CGC CTA CAT GCG CCC ACT AGC CGT GGA GGG GCA      2208
Met Leu Asp Ala His Arg Leu His Ala Pro Thr Ser Arg Gly Gly Ala
                725                    730                    735

TCC GTG GAG GAG ACG GAC CAA AGC CAC TTG GCC ACT GCG GGC TCT ACT      2256
Ser Val Glu Glu Thr Asp Gln Ser His Leu Ala Thr Ala Gly Ser Thr
            740                    745                    750

TCA TCG CAT TCC TTG CAA AAG TAT TAC ATC ACG GGG GAG GCA GAG GGT      2304
Ser Ser His Ser Leu Gln Lys Tyr Tyr Ile Thr Gly Glu Ala Glu Gly
        755                    760                    765

TTC CCT GCC ACA GTC TGA                                              2322
Phe Pro Ala Thr Val
    770
```